United States Patent [19]

Ogawa et al.

[11] Patent Number: 4,898,867
[45] Date of Patent: Feb. 6, 1990

[54] THIENOPYRIMIDINE DERIVATIES AS ALDOSE-REDUCTASE INHIBITORS

[75] Inventors: Kazuo Ogawa, Tokushima; Ichiro Yamawaki; Yoichi Matsushita, both of Tokushima; Naruo Nomura, Naruto; Issei Okazaki, Tokushima, all of Japan

[73] Assignee: Taiho Pharmaceutical Company, Limited, Tokyo, Japan

[21] Appl. No.: 377,862

[22] PCT Filed: Sep. 16, 1988

[86] PCT No.: PCT/JP88/00935

§ 371 Date: May 4, 1989

§ 102(e) Date: May 4, 1989

[87] PCT Pub. No.: WO89/02432

PCT Pub. Date: Mar. 23, 1989

[30] Foreign Application Priority Data

Sep. 16, 1987 [JP] Japan .................................. 62-231425

[51] Int. Cl.$^4$ .................. A61K 31/505; C07D 239/00; C07D 491/00
[52] U.S. Cl. .................... 514/258; 544/250; 544/278; 514/267
[58] Field of Search ................ 544/250, 278; 514/258, 514/267

[56] References Cited

U.S. PATENT DOCUMENTS 4,701,528 10/1987 Thompson et al. ................. 544/250

Primary Examiner—Mary C. Lee
Assistant Examiner—Robert C. Whittenbaugh
Attorney, Agent, or Firm—Armstrong, Nikaido, Marmelstein, Kubovcik & Murray

[57] ABSTRACT

The present invention provides thienopyrimidine derivatives of the formula (I)

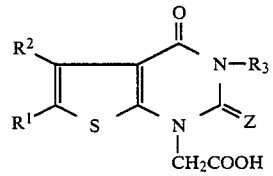

wherein $R_1$ and $R_2$ are the same or different and each represent hydrogen, halogen, lower alkyl, cycloalkyl or phenyl, $R_1$ and $R_2$ taken together may form a ring of an alkylene chain, $R_3$ represents lower alkyl or a group of the formula

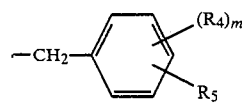

(in which $R_4$ is a lower alkyl, lower alkoxy or halogen, m is 0, 1 or 2, and $R_5$ is hydrogen or halogen) and Z is oxygen or sulfur, or pharmaceutically acceptable salts thereof, pharmaceutical compositions containing them as an active principle and aldose-reductase inhibitors.

5 Claims, No Drawings

THIENOPYRIMIDINE DERIVATIES AS ALDOSE-REDUCTASE INHIBITORS

DESCRIPTION

1. Technical Field

The present invention relates to novel thienopyrimidine derivatives or pharmaceutically acceptable salts thereof, pharmaceutical compositions containing the same and aldose-reductase inhibitors.

2. Background Art

Kinoshita et al. reported that the aldose-reductase participates in crisis and development of complications of diabetes such as diabetic cataract, diabetic neuropathy, diabetic nephropathy and diabetic retinopathy (J. H. Kinoshita et al., Journal of the American Medical Association, 246, 257, (1981)). The aldose-reductase reduces aldoses such as glucose and galactose to polyols such as sorbitols. The polyol produced is relatively stable and rarely passes extracellularly, consequently accumulating intracellularly. Since the hyperglycemic status as in diabetes, promotes the activity of aldose-reductase, the polyols accumulate excessively in the lenses, neurons, vascular tissues, etc. Therefore, the osmotic pressure increases in these tissue cells, which results in swell of the tissues, damaged cellular function and tissue disorders. In view of these situations, it has been desired to develop compounds useful for remedy and prevention of various diabetic complications and excellent in aldose-reductose inhibiting activity by inhibiting the aldose-reductase and thus avoiding abnormal intracellular accumulation of polyols.

DISCLOSURE OF THE INVENTION

The inventors conducted extensive research in view of the above problems of the prior art and found that the novel thienopyrimidine derivatives represented below by the formula (I) and their salts exhibit outstanding aldose-reductase inhibitory effect and are useful as medicaments. Therefore, the invention has been accomplished.

The present invention provides thienopyrimidine derivatives of the formula (I)

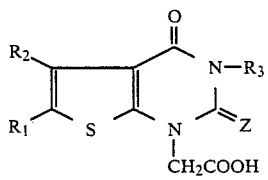

wherein $R_1$ and $R_2$ are the same or different and each represent hydrogen, halogen, lower alkyl, cycloalkyl or pheny, $R_1$ and $R_2$ taken together may form a ring with an alkylene chain, $R_3$ represents lower alkyl or a group of the formula

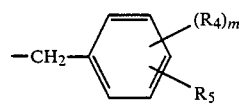

(in which $R_4$ is lower alkyl, lower alkoxy or halogen, m is 0, 1 or 2, and $R_5$ is hydrogen or halogen) and Z is oxygen or sulfur, or pharmaceutically acceptable salts thereof.

Examples of halogen atoms represented by $R_1$, $R_2$, $R_4$ and $R_5$ in the formula (I) are fluorine, chlorine, bromine and iodine. Examples of lower alkyl groups represented by $R_1$, $R_2$, $R_3$ and $R_4$ are straight chain or branched chain $C_1$-$C_6$ alkyl groups such as methyl, ethyl, propyl, isopropyl, butyl, isobutyl, sec-butyl, tert-butyl, pentyl, isopentyl, neopentyl, tert-pentyl, hexyl and isohexyl. Examples of cycloalkyl groups represented by $R_1$ and $R_2$ are $C_3$-$C_7$ cyclopropyl, cyclobutyl, cyclohexyl, etc. Examples of rings with an alkylene chain formed by $R_1$ and $R_2$ taken together are

etc. Examples of lower alkoxy groups represented by $R_4$ are straight chain or branched chain $C_1$-$C_6$ alkoxy groups such as methoxy, ethoxy, propoxy, isopropoxy, butoxy, isobutoxy, tert-butoxy, pentoxy and hexyloxy.

The salts of the compounds of the present invention are pharmaceutically acceptable salts thereof including salts of alkali metals such as sodium, potassium and lithium; salts of alkaline earth metals such as calcium and magnesium; salts of ammonium; salts of tetraalkylammoniums such as tetramethylammonium, tetraethylammonium, tetrapropylammonium and tetrabutylammonium; salts of mono-, di- or trialkylamines such as methylamine, ethylamine, isopropylamine, tert-butylamine, dimethtylamine, diethylamine, trimethylamine and triethylamine; salts of cycloalkylamines such as cyclopentylamine and cyclohexylamine; salts of phenyl(lower alkyl)amines such as benzylamine, phenethylamine and phenylpropylamine; salts of 5- or 6-membered heterocyclic compounds containing in its ring structure one or two nitrogen atoms as the heteroatom such as piperidine, piperazine, imidazoline and pyrrole; salts of mono-, di- or trialkanolamines such as monoethanolamine, monopropanolamine, diethanolamine and triethanolamine; salts of basic amino acids such as lysine, arginine and histidine; organic amines such as tris(-hydroxymethyl)aminomethane; etc.

Of the compounds of the formula (I), preferable are the compounds in which $R_1$ is hydrogen, methyl, isopropyl or halogen, $R_2$ is hydrogen or methyl, $R_3$ is 3,4-dichlorobenzyl, 2,4-dichlorobenzyl or 4-bromo-2-fluorobenzyl, and Z is oxygen or sulfur. Most preferable are the compounds of the formula (I) in which $R_1$ is isopropyl, chlorine or bromine, $R_2$ is hydrogen, $R_3$ is 4-bromo-2-fluorobenzyl, and Z is oxygen.

The compounds of the present invention of the formula (I) and the pharmaceutically acceptable salts thereof display excellent aldose-reductase inhibitory effects and are useful as a medicament, especially for treating chronic syndromes and complications due to diabetes.

Therefore, the present invention provides an aldose-reductase inhibitor containing an effective amount of the compound of the formula (I) or a pharmaceutically acceptable salt thereof and a pharmacological carrier.

The present invention also provides a method of inhibiting aldose-reductase comprising administrating to patients an effective amount of the compound of the formula (I) or a pharmaceutically acceptable salt thereof.

The thienopyrimidine derivative of the present invention of the formula (I) in which Z is oxygen can be prepared by the process as shown below in Reaction scheme (1). When one or both of $R_1$ and $R_2$ in the above formula (I) are halogen, the compound can be prepared by the process as shown below in Reaction scheme (1) or (2). The compound of the formula (I) wherein Z is sulfur can be prepared by the process as shown below in Reaction scheme (3).

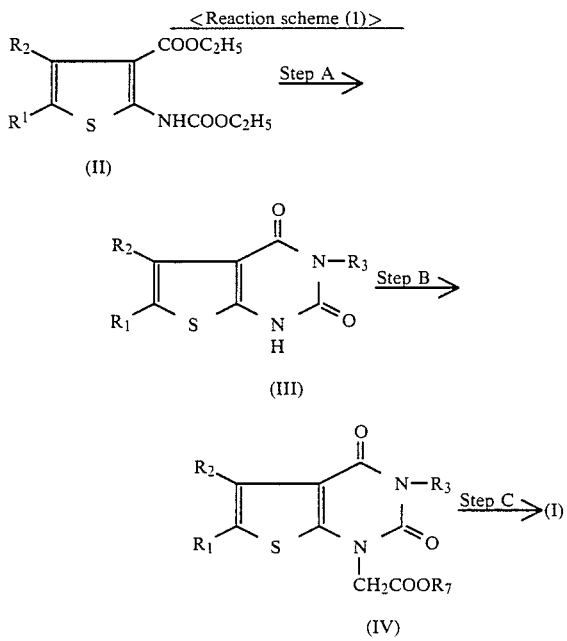

In the foregoing formulas, $R_1$, $R_2$ and $R_3$ are as defined above, and $R_7$ is a carboxyl-protecting group.

The compound of the formula (II) is known and described, for example, in "Heterocyclic Compounds", vol. 44. part 3, pp 565–973 "Thiophene and its derivatives", written by John M. Barker and Patrick R. Huddleston, edited by Salo Gronowitz, published by John Wiley & Sons, Inc., New York (1986).

Generally used as carboxyl-protecting groups represented by $R_7$ are known groups, for example, subtituted or unsubstituted alkyl groups such as methyl, ethyl, propyl, butyl, tert-butyl and trichloroethyl; substituted or unsubstituted aralkyl groups such as benzyl, diphenylmethyl, p-nitrobenzyl and p-methoxybenzyl; acyloxyalkyl groups such as acetoxymethyl, acetoxyethyl, propionyloxyethyl, pivaloyloxymethyl, pivaloyloxypropyl, benzoyloxymethyl, benzoyloxyethyl, benzylcarbonyloxymethyl and cyclohexylcarbonyloxymethyl; alkoxyalkyl groups such as methoxymethyl, ethoxymethyl and benzyloxymethyl; and other groups such as tetrahydropyranyl, dimethylaminoethyl, dimethylchlorosilyl and trichlorosilyl.

Each step in the above scheme can be done as described below in more detail.

Step A

The thiophene derivative of the formula (II) is allowed to react with an amine of the formula $R_3NH_2$ (V)

(in which $R_3$ is as defined above) in the presence or absence of a base in a suitable solvent, giving the thienopyrimidine derivative of the formula (III).

Examples of the amine of the formula (V) are methylamine, ethylamine, propylamine, isopropylamine, pentylamine, hexylamine, benzylamine, 4-chlorobenzylamine, 2,4-dichlorobenzylamine, 3,4-dichlorobenzylamine, 4-methoxybenzylamine, 4-methylbenzylamine, 2-fluoro-4-bromobenzylamine, 2,4-difluorobenzylamine, etc. Although the solvent is not specifically limited insofar as it does not participate in this reaction, it is preferred to use alcohols such as methanol, ethanol, propanol and isopropanol; N,N-dimethylformamide; N,N-acetylacetamide; ethers such as tetrahydrofuran and dioxane; or the mixture of these solvents. Examples of bases useful in this reaction are alkoxides of alkali metals or alkaline earth metals such as sodium methoxide, potassium methoxide, potassium t-butoxide, sodium ethoxide, sodium isopropoxide and magnesium methoxid; hydrides such as sodium hydride, potassium hydride and lithium hydride; amide compounds such as lithium diisopropylamide, lithium dicyclohexylamide, sodium amide and potassium amide; organic bases such as triethylamine, 4-(N,N-dimethylamino)pyridine and hydroxypyridine; etc. The base is preferably used in an amount of about 1.0–1.5 moles per mole of the amine (V). Although the proportions of the thiophene derivative (II) and the amine (V) may be appropriately determined, in general the amine (V) is preferably used in an amount of about 1.0–2.0 moles per mole of the thiophene derivative (II). The reaction is usually conducted with heating at a temperatuare of about 60°–300° C., preferably at a temperature of about 200°–250° C.

Step B

The thienopyrimidine derivative of the formula (III) is allowed to react with an acetic acid derivative of the formula $XCH_2 COOR_7$ (VI)

(in which $R_7$ is as defined above, and X is chlorine, bromine or iodine) in the presence of a base in a suitable solvent, giving the thienopyrimidine acetate derivative of the formula (IV). Although the solvent is not specifically limited insofar as it does not participate in this reaction, it is preferred to use ethers such as diethyl ether, tetrahydrofuran, dimethoxyethane and dioxane, aromatic hydrocarbons such as benzene, toluene and xylene, N,N-dimethylformamide, N,N-dimethylacetamide, dimethylsulfoxide or the like.

Examples of useful bases are alkoxides of alkali metals or alkaline earth metals such as potassium methoxide, potassium ethoxide, potassium t-butoxide, sodium methoxide, sodium ethoxide, sodium propoxide, sodium isopropoxide, lithium methoxide and magnesium ethoxide; hydrides such as potassium hydride, sodium hydride and lithium hydride; amide compounds such as sodium amide, lithium amide, potassium amide and lithium diisopropylamide; hydroxides such as potassium hydroxide, sodium hydroxide, lithium hydroxide and calcium hydroxide; carbonates such as potassium carbonate and sodium carbonate; etc. The base is preferably used in an amount of about 1.0–1.5 moles per mole of the acetic acid derivative (VI). Although the proportions of the thienopyrimidine derivative (III) and the acetic acid derivative (VI) can be appropriately determined, in general the acetic acid derivative (VI) is preferably used in an amount of about 1.0–2.0 moles per mole of the thienopyrimidine derivative (III). Although the reaction temperature is not specifically limited, the reaction is usually conducted with cooling or at room temperature.

Step C

The thienopyrimidine acetate derivative of the formula (IV) obtained is subjected to de-esterification reaction with or without isolation from the reaction system of Step B, giving the thienopyrimidine derivative of the formula (I). The de-esterification is conducted by a conventional method, for example, by a method using acid or base, etc.

Examples of acids useful in a method using acid are lower fatty acids such as formic acid, acetic acid and propionic acid, trihaloacetic acids such as trichloroacetic acid and trifluoroacetic acid, halogenated hydroacids such as hydrochloric acid, hydrobromic acid and hydrofluoric acid, organic sulfonic acids such as p-toluenesulfonic acid and trifluoromethanesulfonic acid; and mixtures thereof.

When an acid in the liquid form is used in the above reaction with an acid, no other solvent is required, but a solvent which does not participate in the reaction can be used, for example, halogenated hydrocarbons such as dichloromethane, chloroform and 1,2-dichloroethane, cyclic ethers such as tetrahydrofuran and dioxane, N,N-dimethylformamide, acetone, water and mixtures thereof.

Examples of bases useful in a method using a base are hydroxides of alkali metals or alkaline earth metals such as lithium hydroxide, sodium hydroxide, potassium hydroxide, barium hydroxide, calcium hydroxide and magnesium hydroxide, carbonates such as potassium carbonate and sodium carbonate, 1,8-diazabicyclo[5,4,0]-7-undecene, etc. As a solvent, those which do not participate in the reaction are used, for example, alcohols such as methanol, ethanol and isopropanol, ethers such as tetrahydrofuran, dimethoxyethane and dioxane, N,N-dimethylformamide, mixtures of the aforementioned solvents and/or water, etc.

In the above Reaction scheme (1), the compound (III) can be also synthesized from the thiophene derivative of the formula (II') by the process as shown in the following reaction scheme.

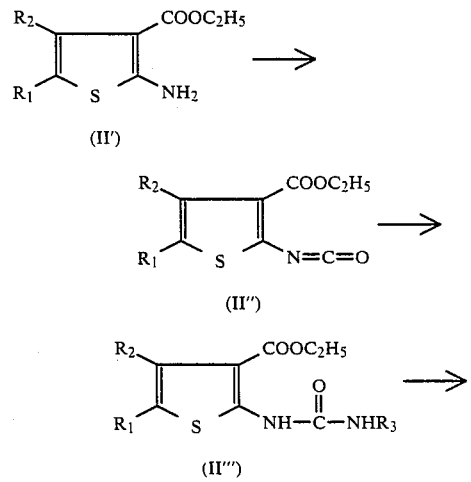

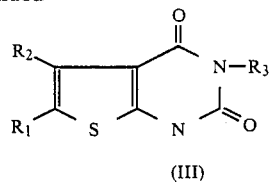

In the foregoing formulas, $R_1$, $R_2$ and $R_3$ are as defined above.

The compound of the formula (II') is knowm and described, for example, in "Heterocyclic Compounds", vol. 44. part 3, pp 565-973 "Thiophene and its derivatives", written by John M. Barker and Patrick R. Huddleston, edited by Salo Gronowitz, published by John Wiley & Sons, Inc., New York (1986).

The thiophene derivative of the formula (II') is heated to 50°-120° C. in the presence of phosgene or trichloromethyl chloroformate in a suitable solvent, and then the solvent is distilled off, giving the isocyanate derivative (II''). Examples of useful solvents are aromatic hydrocarbons such as xylene, toluene and benzene, halogenated hydrocarbons such as chloroform, 1,2-dichloroethane and tetrachloromethane, esters such as ethyl acetate and isopropyl acetate, cyclic ethers such as dioxane and tetrahydrofuran, dimethoxyethane and like solvents which do not participate in the reaction. The compound (II'') is allowed to react with the amine of formula (V) in a solvent, giving the ureide derivative (II'''). Solvents suitable for the reaction are ethers such as diethyl ether, diisopropyl ether, tetrahydrofuran and dioxane, aromatic hydrocarbons such as xylene, toluene, benzene and chlorobenzene, halogenated hydrocarbons such as chloroform, 1,2-dichloroethane, tetrachloromethane and dichloromethane, etc. Although the reaction usually proceeds exothermically at room temperature, at the conclusion of the reaction the reaction system may be heated or such as a base may be as 4-(N,N-dimethylamino)pyridine, pyridine, triethylamine, N-methylpiperidine, diisopropylethylamine, dicyclohexylethylamine, etc. The base is used in an amount of 0.1-3.0 equivalents per equivalent of the amine (V). The amount of the amine (V) is appropriately determined, but it is usually preferable to use the amine (V) in an amount of about 1.0 to about 2.0 moles per mole of the thiophene derivative (II''). The resulting ureide derivative (II''') is subjected to cyclization in a suitable solvent as it is or in the presence of a base, giving the thienopyrimidine derivative of the formula (III). As a base are exemplified organic amines such as triethylamine, pyridine, N-methylpiperidine, diisopropylethylamine and dicyclohexylethylamine, hydroxides of alkali metals such as sodium hydroxide and potassium hydroxide, alkoxides of alkali metals such as sodium methoxide, sodium ethoxide, sodium isopropoxide, potassium methoxide, potassium ethoxide, potassium t-butoxide and lithium methoxide, hydrides of alkali metals such as potassium hydride, lithium hydride and sodium hydride and other usual bases. Suitably used as a solvent are alcohols such as methanol, ethanol, propanol, isopropanol and butanol, ethers such as tetrahydrofuran, dimethoxyethane and dioxane, amides such as N,N-dimethylformamide and N,N-dimethylacetamide, dimethylsulfoxide or mixtures thereof. The base is preferably used in an amount of about 1.0-3.0 moles per mole of the ureide derivative. The reaction is carried out usually at a temperature of about 50° to about 150° C.

<Reaction Scheme (2)>

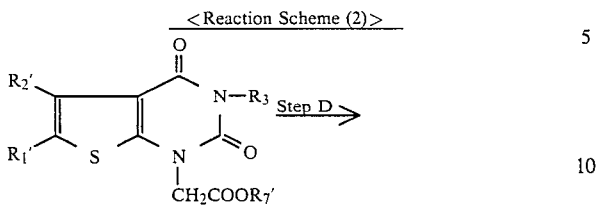

(IV')

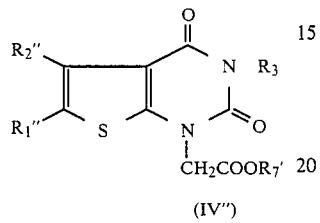

(IV'')

In the foregoing formulas, $R_1'$ and $R_2'$ are the same as $R_1$ and $R_2$ provided that at least one of them is hydrogen, $R_7'$ is hydrogen or the same as $R_7$, $R_1''$ and $R_2''$ and the same as $R_1$ and $R_2$ provided that at least one of them is halogen, and $R_3$ and $R_7$ are as defined above.

Step D

The compound of the formula (IV') in which one or two hydrogen atoms exist in the thiophene ring moiety of the compound (IV) can be halogenated at the thiophene ring by a conventional method generally used in halogenating a thiophene. This procedure gives the compound of the formula (IV''') or (I) in which one or two halogen atoms exist in the thiophene ring moiety. The halogenation is conducted by causing such a halogenating agent to act as chlorine, sulfuryl chloride, bromine and iodine in the presence or the absence of a catalyst in a solvent which does not participate in the reaction. Suitable solvents include acetic acid, ethers such as ethyl ether and dioxane, halogenated hydrocarbons such as chloroform, 1,2-dichloroethane, tetrachloromethane and dichloromethane, water or mixtures thereof. In this case, the reaction temperature is not limited specifically. Examples of catalysts are inorganic acids such as sulfuric acid and periodic acid, Lewis acids such as alminium chloride, mercury chloride and tin chloride and the like. The halogenation is also suitably carried out by reacting the compound (IV') with a N-halogenosuccinimide such as N-chlorosuccinimide or N-bromosuccinimide as a halogenating agent in the above solvent at a temperature between room temperature and the reflux temperature of the solvent. The halogenating agent is generally used in an amount of about 1.0 to about 2.5 moles per mole of the compound (IV'). The compound of the formula (IV'') can be made into the compound (I) by the method at Step C in Reaction scheme (1).

<Reaction Scheme (3)>

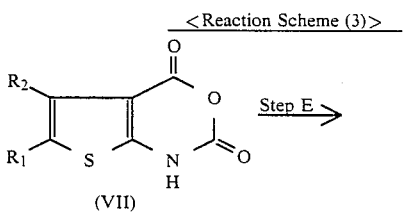

(VII)

-continued
<Reaction Scheme (3)>

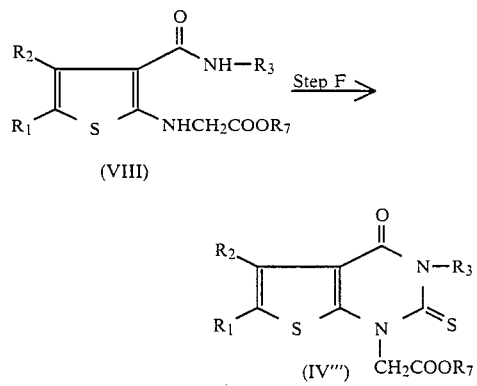

(VIII)

(IV''')

In the foregoing formulas, $R_1$, $R_2$, $R_3$ and $R_7$ are as defined above.

Step E

One to two equivalents of sodium hydride is added to a solution of the compound of the formula (VII) in N,N-dimethylformamide at a temperature of below room temperature, and the mixture is allowed to react with the acetic acid derivative (VI). Then the amine of the formula (V) is added and the mixture is allowed to react at a temperature between room temperature and 100° C. to obtain the compound of the formula (VIII). The compounds of the formulas (VI) and (V) are preferably used in amounts of about 1.0 to about 2.0 moles per mole of the compound (VII).

The compound of the formula (VII) can be prepared according to a conventional method for preparing isatonic anhydride by reacting the known corresponding 2-amino-3-thiophenecarboxylic acid ("Heterocyclic Compounds" vol. 44. part 3, pp 565-973 "Thiophene and its derivatives", written by John M. Barker and Patrick R. Huddleston, edited by Salo Gronowitz, published by John Wiley & Sons, Inc., New York (1986)) with phosgene or trichloromethyl chloroformate. The method using phosgene is described, for example, in E. C. Wagner and M. F. Fegley. Organic Synthesis, vol. III, 488 (1955). The method using trichloromethyl chloroformate is described, for example, in K. Kurita, T. Matsumura and Y. Iwakura, Journal of Organic Chemistry, vol. 41, 2070 (1976).

Step F

One mole of the compound of the formula (VIII) and 2 to 3 moles of 1,1'-thiocarbonyldiimidazole are dissolved in dioxane. The solution is heated to a bath temperature of 150° C. and allowed to react for one to four hours, giving the thienopyrimidine derivative of the formula (IV'''). The compound can be treated in the same manner as in Step C in Reaction scheme (1) to give a compound of the formula (I).

The novel thienopyrimidine derivative of the present invention produced by the above reaction can be easily isolated by a conventional separation method, for example, recrystallization, column chromatography or the like.

For use in preventing or treating the diseases caused by aldose-reductase, e.g., diabetic cataract, neuropathy, nephropathy, diabetic retinopathy, the thienopyrimidine derivatives of the present invention are administered to mammals including humans in any of pharmaceutical dosage forms including oral preparation, injection, suppository and eye drop. Such preparations can be formulated in a manner already known in the art.

For the formulation of solid preparations for oral administration such as tablets, coated tablets, granules, powders and capsules, an excipient and, when required, a binder, disintegrator, lubricant, coloring agent, corrigent, flavor, etc. are added to the compound of the invention, and then a preparation is formulated in a usual manner. Such additives are those already known in the art, and usuful examples are excipients such as lactose, sucrose, sodium chloride, glucose solution, starch, calcium carbonate, kaolin, crystalline cellulose and silicic acid; binders such as water, ethanol, propanol, glucose, carboxymethyl cellulose, hydroxymethyl cellulose, methyl cellulose, ethyl cellulose, schellac, potassium phosphate and polyvinyl pyrrolidone; disintegrators such as dried starch, sodium alginate, agar powder, sodium hydrogencarbonate, calcium carbonate, sodium lauryl sulfate, glyceryl monostearate and lactose; lubricants such as purified talc, stearic acid salt, boric acid powder and polyethylene glycol; corrigents such as sucrose, orange peel, citric acid and tartaric acid, etc.

For the formulation of liquid preparations for oral administration such as oral liquid preparations and syrups, a corrigent, buffer, stabilizer, flavor, etc. can be added to the compound of the present invention, whereafter a preparation can be formulated in a usual manner. Examples of useful corrigents are those exemplified above. Examples of buffers are sodium citrate, etc. Examples of stabilizers are tragacanth, gum arabic, gelatin, etc.

Parenteral preparations such as a subcutaneous injection, intramuscular injection, intravenous injection or the like can be prepared in a usual manner by adding to the comopound of the invention a pH adjusting agent, buffer, stabilizer, isotonic agent, local anesthetic, etc. Examples of pH adjusting agents and buffers are sodium citrate, sodium acetate, sodium phosphate, etc. Examples of stabilizers are sodium pyrosulfite, EDTA, thioglycolic acid, thiolactic acid, etc. Examples of local anesthetics are procaine hydrochloride, lidocaine hydrochloride, etc.

Suppositories can be prepared in a usual manner by adding excipients such as unsaturated fatty acid triglycerides and, if required, surfactants such as Tween.

Eye drops can be prepared in a usual manner by using a diluent such as distilled water and physiological saline. Eye drops should preferably be made isotonic by using a pH adjusting agent, buffer, etc.

The amount of the compound of the present invention to be incorporated into each dosage form varies with the symptoms of the patient or with the type of the preparation. Preferably the amount per administration unit is about 10 to about 300 mg for oral administration, about 10 to about 50 mg for pareteral administration, about 10 to 200 mg for intrarectal administration and about 5 to about 50 mg for administration to eyes. The dosage per day of such preparations is variable with the symptoms, body weight, age, sex and the like of the patient. Usually the preparation is adminstered to an adult in an amount of about 5 to about 900 mg per day based on the compound, preferably in one or two to four devided doses.

The present invention will be described below in more detail with reference to Reference Examples and Examples.

REFERENCE EXAMPLE 1

Preparation of 3-(4-chlorobenzyl)-5,6-dimethylthieno[2,3-d]pyrimidin-2,4(1H,3H)-dione (Compound III-1)

A 1 g quantity of ethyl 2-ethoxycarbonylamino-4,5-dimethyl-3-thiophenecarboxylate and 1 g of 4-chlorobenzylamine were dissolved in a mixture of 3 ml of ethanol and 1 ml of N,N-dimethylformamide and the mixture was allowed to react in a sealed tube at 230° C. for 7 hours. The reaction mixture was concentrated and the residue was recrystallized from an acetone-ethanol-dimethylformamide mixture, giving 0.8 g of 3-(4-chlorobenzyl)-5,6-dimethylthieno[2,3-d]pyrimidin-2,4(1H,3H)-dione having a melting point of 291° to 292° C. in a yield of 68%.

| Elemental Analysis (for $C_{15}H_{13}N_2O_2SCl$) | | | |
|---|---|---|---|
| | C | H | N |
| Calcd. (%): | 56.16 | 4.08 | 8.73 |
| Found (%): | 56.12 | 4.00 | 8.83 |

REFERENCE EXAMPLE 2

The compounds III-2 to III-9 as shown below in Table 1 were prepared in the same manner as in Reference Example 1.

REFERENCE EXAMPLE 3

Preparation of 3-(4-bromo-2-fluorobenzyl)-5-methylthieno[2,3-d]-pyrimidine-2,4(1H,3H)-dione (Compound III-17)

A solution of 3.71 g of ethyl 2-amino-4-methyl-3-thiophenecarboxylate and 7.91 g of trichloromethyl chloroformate in 50 ml of dioxane was stirred at a bath temperature of 80° to 100° C. for 3 hours, and the solvent was evaporated off under reduced pressure. The residue was dissolved in 30 ml of diethyl ether and 4.49 g of 4-bromo-2-fluorobenzylamine was added dropwise thereto with ice-cooling. After the temperature of the mixture was raised to room temperature, the mixture was stirred for three hours, 20 ml of n-hexane was added dropwise thereto and a colorless precipitate was collected, giving 5.4 g of the ureide compound of the following formula in a yield of 68%.

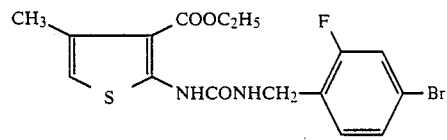

A 5.3 g quantity of the ureide compound was dissolved in 70 ml of ethanol and 1.58 g of sodium methoxide was added thereto. The mixture was refluxed for 5 hours, concentrated to a half of volume, and then homogeneously mixed with 20 ml of water. The resulting solution was neutralized and acidified with concentrated hydrochloric acid to precipitate colorless crystals. The crystals were collected by filtration, washed with water and dried in vacuo, giving 4.75 g of the compound III-17 having a melting point of 296° to 297.5° C. in a yield of 97%.

| Elemental Analysis (for $C_{14}H_{10}N_2O_2SBrF$) | | | |
|---|---|---|---|
| | C | H | N |
| Calcd. (%): | 45.54 | 2.73 | 7.59 |
| Found (%): | 45.51 | 2.61 | 7.64 |

REFERENCE EXAMPLE 4

The compounds III-10 to III-16, III-18 and III-19 as shown below in Table 1 were prepared in the same manner as in Reference Example 3.

TABLE 1 structure (III): thiophene ring with $R_1$ at 5-position (attached to S), $R_2$ at 4-position, a C(=O)-N(R_3)-C(=O)-NH group forming a fused ring at the 2,3-positions

| Compound No. | $R_1$ | $R_2$ | $R_3$ | Yield (%) | mp (°C.) |
|---|---|---|---|---|---|
| III-1 | $CH_3$ | $CH_3$ | $CH_2$-C$_6$H$_4$-Cl (4-Cl) | 68 | 291~292 |
| III-2 | $CH_3$ | $CH_3$ | $CH_2$-C$_6$H$_3$(2-Cl)(4-Cl) | 70 | 275~276 |
| III-3 | $(CH_3)_2CH$ | H | $CH_2$-C$_6$H$_3$(2-Cl)(4-Cl) | 43 | 252.5~253.5 |
| III-4 | $(CH_3)_2CH$ | H | $CH_2$-C$_6$H$_3$(2-Cl)(4-Cl) | 12 | 223~226 |
| III-5 | H | $CH_3$ | $CH_2$-C$_6$H$_3$(2-Cl)(4-Cl) | 70 | 299~300 |
| III-6 | cyclohexyl | | $CH_2$-C$_6$H$_4$-OCH$_3$ (4-OCH$_3$) | 29 | 230~232 |
| III-7 | cyclohexyl | | $CH_2$-C$_6$H$_4$-CH$_3$ (4-CH$_3$) | 40 | 240~241 |
| III-8 | cyclohexyl | | $CH_2$-C$_6$H$_3$(2-Cl)(4-Cl) | 45 | 255~256 |
| III-9 | cyclohexyl | | $(CH_2)_5CH_3$ | 24 | 132~132.5 |

TABLE 1-continued
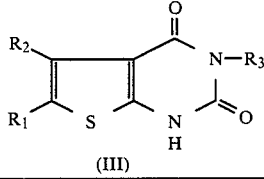
(III)
| No. | R₁ | R₂ | R₃ | Yield (%) | m.p. (°C) |
|---|---|---|---|---|---|
| III-10 | CH₃ | H | 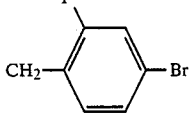 | 55 | 304~305 |
| III-11 | CH₃ | CH₃ | 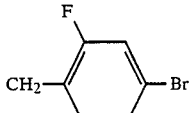 | 47 | 258~258.5 |
| III-12 | 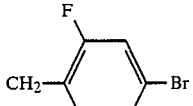 | | 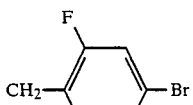 | 49 | 225~230 |
| III-13 | 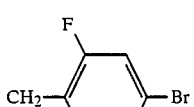 | H | 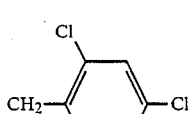 | 69 | 257~259 |
| III-14 | (CH₃)₂CH | H | 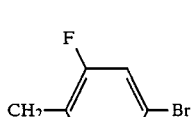 | 76 | 227~228 |
| III-15 | (CH₃)₃C | H | 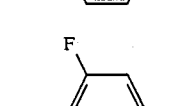 | 43 | 263.5~265 |
| III-16 | H | H | 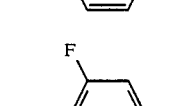 | 71 | 290~291 |
| III-17 | H | CH₃ | 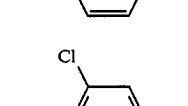 | 66 | 296~297.5 |
| III-18 | (CH₃)₂CH | H | (2,4-difluorobenzyl) | 64 | 219~221 |
| III-19 | (cyclopentyl) | H | (2,4-dichlorobenzyl) | 50 | 257~259 |

TABLE 1-continued $$\text{(III)}$$ structure with R_2, R_1, S, N-R_3, carbonyl groups, NH

| Compound No. | Molecular Formula | Elemental Analysis(%): Calcd. in parenthesis | | |
|---|---|---|---|---|
| | | C | H | N |
| III-1 | $C_{15}H_{13}N_2O_2ClS$ | (56.16) | (4.08) | (8.73) |
| | | 56.12 | 4.00 | 8.83 |
| III-2 | $C_{15}H_{12}N_2O_2Cl_2S$ | (50.72) | (3.40) | (7.89) |
| | | 50.43 | 3.26 | 7.80 |
| III-3 | $C_{16}H_{14}N_2O_2Cl_2S$ | (52.04) | (3.83) | (7.59) |
| | | 52.01 | 3.87 | 7.60 |
| III-4 | $C_{16}H_{14}N_2O_2Cl_2S$ | (52.04) | (3.83) | (7.59) |
| | | 51.75 | 3.81 | 7.51 |
| III-5 | $C_{14}H_{10}N_2O_4S$ | (62.21) | (3.73) | (10.36) |
| | | 62.10 | 3.54 | 10.20 |
| III-6 | $C_{18}H_{18}N_2O_3S$ | (63.14) | (5.30) | (8.18) |
| | | 63.28 | 5.11 | 8.17 |
| III-7 | $C_{18}H_{18}N_2O_2S$ | (66.23) | (5.56) | (8.58) |
| | | 66.30 | 5.42 | 8.50 |
| III-8 | $C_{17}H_{14}Cl_2N_2O_2S$ | (53.55) | (3.70) | (7.35) |
| | | 53.45 | 3.77 | 7.37 |
| III-9 | $C_{16}H_{22}N_2O_2S$ | (62.72) | (7.24) | (9.14) |
| | | 62.50 | 7.12 | 9.02 |
| III-10 | $C_{14}H_{10}BrFN_2O_2S$ | (45.54) | (2.73) | (7.59) |
| | | 45.86 | 3.04 | 7.51 |
| III-11 | $C_{15}H_{12}BrFN_2O_2S$ | (47.01) | (3.16) | (7.31) |
| | | 47.11 | 3.18 | 7.41 |
| III-12 | $C_{17}H_{14}FBrN_2O_2S$ | (49.89) | (3.45) | (6.84) |
| | | 49.49 | 3.20 | 6.76 |
| III-13 | $C_{18}H_{16}BrFN_2O_2S$ | (51.07) | (3.81) | (6.62) |
| | | 50.86 | 3.84 | 6.63 |
| III-14 | $C_{16}H_{14}BrFN_2O_2S$ | (48.38) | (3.55) | (7.05) |
| | | 48.18 | 3.56 | 7.11 |
| III-15 | $C_{17}H_{16}Cl_2N_2O_2S$ | (53.27) | (4.21) | (7.31) |
| | | 53.58 | 4.37 | 7.31 |
| III-16 | $C_{13}H_8BrFN_2O_2S$ | (43.96) | (2.27) | (7.89) |
| | | 44.05 | 2.30 | 7.83 |
| III-17 | $C_{14}H_{10}BrFN_2O_2S$ | (45.54) | (2.73) | (7.59) |
| | | 45.51 | 2.61 | 7.64 |
| III-18 | $C_{16}H_{14}F_2N_2O_2S$ | (57.13) | (4.20) | (8.33) |
| | | 57.63 | 4.42 | 8.53 |
| III-19 | $C_{16}H_{18}Cl_2N_2O_2S$ | (54.69) | (4.08) | (7.09) |
| | | 54.70 | 4.18 | 6.99 |

REFERENCE EXAMPLE 5

Preparation of 3-(4-chlorobenzyl)-1-ethoxycarbonylmethyl-5,6-dimethylthieno[2,3-d]pyrimidin-2,4(1H,3H)-dione (Compound IV-1)

A 0.6 g quantity of 3-(4-chlorobenzyl)-5,6-dimethylthieno[2,3-d]pyrimidin-2,4(1H,3H)-dione (Compound III-1) was dissolved in 20 ml of anhydrous N,N-dimethylformamide. To the solution were added at room temperature 0.1 g of 50% sodium hydride and then 0.4 g of ethyl bromoacetate. The mixture was stirred at room temperature for 17 hours, concentrated and acidified by adding diluted hydrochloric acid with ice-cooling. The crystals precipitated were collected by filtration and recrystallized from ethanol, giving 0.7 g of 3-(4-chlorobenzyl)-1-ethoxycarbonylmethyl-5,6-dimethylthieno[2,3-d]pyrimidin-2,4(1H,3H)-dione having a melting point of 151° to 152° C. in a yield of 92%.

| Elemental Analysis (for $C_{19}H_{19}N_2O_4SCl$) | | | |
|---|---|---|---|
| | C | H | N |
| Calcd. (%): | 56.09 | 4.71 | 6.88 |
| Found (%): | 55.84 | 4.50 | 6.89 |

REFERENCE EXAMPLE 6

The compounds IV-2 to IV-8 and IV-12 to IV-22 as shown below in Table 2 were prepared in the same manner as in Reference Example 5.

REFERENCE EXAMPLE 7

Preparation of 1-ethoxycarbonylmethyl-3-hexyl-5,6,7,8-tetrahydrobenzothieno[2,3-d]pyrimidin-2,4(1H,3H)-dione (Compound IV-9)

A 1.2 g quantity of 3-hexyl-5,6,7,8-tetrahydrobenzothieno[2,3-d]pyrimidin-2,4(1H,3H)-dione (Compound III-9), 0.14 g of 50% sodium hydride and 1.0 g of ethyl bromoacetate were allowed to react with each other in the same manner as in Reference Example 5. The residue obtained by concentration was subjected to silica gel column chromatography using chloroform as an eluent. Then 1.2 g of 1-ethoxycarbonylmethyl-3-hexyl-5,6,7,8-tetrahydrobenzothieno[2,3-d]pyrimidin-2,4(1H,3H)-dione was obtained in a yield of 77%.

Nuclear Magnetic Resonance (DMSO-d₆): δ(ppm): 0.85 (3H, t), 1.0–2.0 (12H, m), 1.21 (3H, t), 2.5–2.9 (4H, m), 3.84 (2H, t), 4.17 (2H, q), 4.7 (2H, s)

REFERENCE EXAMPLE 8

Preparation of 1-ethoxycarbonylmethyl-3-(3,4-dichlorobenzyl)-6-bromo-5-methylthieno[2,3-d]pyrimidin-2,4(1H,3H)-dione (Compound IV''-10)

A 0.3 g quantity of 1-ethoxycarbonylmethyl-3-(3,4-dichlorobenzyl)-5-methylthieno[2,3-d]pyrimidin-2,4(1H,3H)-dione (compound IV-5) synthesized in Reference Example 6 and 0.137 g of N-bromosuccinimide were dissolved in 30 ml of anhydrous tetrachloromethane, and the mixture was refluxed for 2 hours. The solvent was distilled off under reduced pressure and the residual solid obtained was purified by silica gel column chromatography (eluent:chloroform:n-hexane=2:1) to afford 0.30 g of 1-ethoxycarbonylmethyl-3-(3,4-dichlorobenzyl)-6-bromo-5-methylthieno[2,3-d]pyrimidin-2,4(1H,3H)-dione having m.p. of 165.5° to 167° C. in a yield of 85%.

| Elemental Analysis (for C₁₈H₁₅N₂O₄SBrCl₂) | | | |
| --- | --- | --- | --- |
| | C | H | N |
| Calcd. (%): | 47.21 | 2.99 | 5.53 |
| Found (%): | 47.50 | 2.84 | 5.42 |

REFERENCE EXAMPLE 9

The compound IV''-23 as shown in Table 2 was prepared in the same manner as in Reference Example 8.

REFERENCE EXAMPLE 10

Preparation of 1-ethoxycarbonylmethyl-3-(3,4-dichlorobenzyl)-6-chloro-5-methylthieno[2,3-d]pyrimidin-2,4(1H,3H)-dione (Compound IV''-11)

A 0.427 g quantity of 1-ethoxycarbonylmethyl-3-(3,4-dichlorobenzyl)-5-methylthieno[2,3-d]pyrimidin-2,4(1H,3H)-dione (compound IV-5) synthesized in Reference Example 6 and 0.162 g of sulfuryl chloride were dissolved in 30 ml of anhydrous tetrachloromethane, and the mixture was allowed to react at 50° to 70° C. for 6 hours. The residue obtained by concentration of the reaction mixture was subjected to silica gel column chromatography using a 2:1 mixture of chroloform and n-hexane as an eluent to afford 0.30 g of 1-ethoxycarbonylmethyl-3-(3,4-dichlorobenzyl)-6-chloro-5-methyl-thieno[2,3-d]pyrimidin-2,4(1H,3H)-dione having m.p. of 141° to 145° C. in a yield of 65%.

| Elemental Analysis (for C₁₈H₁₅N₂O₄SCl₃) | | | |
| --- | --- | --- | --- |
| | C | H | N |
| Calcd. (%): | 46.82 | 3.27 | 6.07 |
| Found (%): | 46.65 | 3.12 | 5.92 |

REFERENCE EXAMPLE 11

The compound IV''-24 as shown in Table 2 was prepared in the same manner as in Reference Example 10.

REFERENCE EXAMPLE 12

Preparation of 1-ethoxycarbonylmethyl-3-(4-bromo-2-fluorobenzyl)-6-isopropyl-4(3H)-oxo-2(1H)-thioxothieno[2,3-d]pyrimidine (Compound IV'''-25)

A 7.8 g quantity of 2-amino-5-isopropylthiophenecarboxylic acid and 25 g of trichloromethyl chloroformate were dissolved in 80 ml of dioxane. The resulting solution was refluxed for 6 hours and then the solvent was evaporated off under reduced pressure. The pale brown solids obtained were crushed in ether and the pieces were collected by filtration and dried in vacuo. As pale color solids was obtained 5.6 g of the compound of the following formula in a yield of 74%.

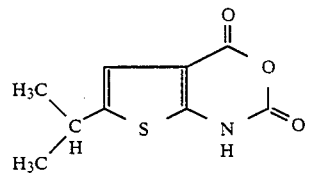

M.p.: 180°–181° C. (CO₂ generated).

| Elemental Analysis (for C₉H₉NO₃S) | | | |
| --- | --- | --- | --- |
| | C | H | N |
| Calcd. (%): | 51.17 | 4.29 | 6.63 |
| Found (%): | 51.21 | 4.36 | 6.65 |

A 5.4 g quantity of this compound was dissolved in 40 ml of N,N-dimethylformamide and 1.45 g of 60% sodium hydride was added to the solution with ice-cooling. After stirring for 40 minutes, 4.34 ml of ethyl bromoacetate was added thereto. The temperature of the mixture was raised to room temperature, and the reaction was conducted for 2 hours. Then 7.96 g of 4-bromo-2-fluorobenzylamine was added to the reaction mixture, the mixture was allowed to react at 80° C. for two hours, 5.4 ml of triethylamine was added thereto and the reaction mixture was allowed to react for 1 hour. The solvent was distilled off under reduced pressure and the residue was extracted with 120 ml of chloroform. The extract was washed with water, dried over anhydrous sodium carbonate and then concentrated. The residue obtained was recrystallized from a mixture of chloroform, iropropyl ether and n-hexane, giving 8.92 g of the compound of the following formula as pale yellow needle crystals in a yield of 65%.

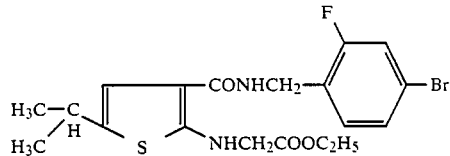

M.p.: 135.5°–137.5° C.

| Elemental Analysis (for C₁₉H₂₂N₂O₃SBrF) | | | |
| --- | --- | --- | --- |
| | C | H | N |
| Calcd. (%): | 49.90 | 4.85 | 6.13 |
| Found (%): | 49.63 | 4.65 | 6.16 |

A 2.29 quantity of this compound and 1.96 g of 1,1'-thiocarbonyldiimidazole were dissolved in 20 ml of dioxane. The dioxane was distilled off with stirring on the bath at 150° C. and the mixture was allowed to react for 2 hours. Ethanol was added to the reaction mixture when hot and the solution was cooled to room temperature. The crystals precipitated were collected and purified by silica gel (75 g) column chromatography using chloroform as an eluent, giving as colorless crystals 2.11 g of Compound IV''''-25 having m.p. of 177° to 179° C. in a yield of 85%.

| Elemental Analysis (for $C_{20}H_{20}N_2O_3S_2BrF$) | | | |
| --- | --- | --- | --- |
| | C | H | N |
| Calcd. (%): | 48.10 | 4.04 | 5.61 |
| Found (%): | 48.30 | 3.94 | 5.64 |

TABLE 2

(IV) — structure: thiophene ring with $R_1$, $R_2$ substituents, S, bearing $-C(O)-N(R_3)-$ and $N(CH_2COOR_7)$ with $=Z$ group.

| Compound No. | $R_1$ | $R_2$ | $R_3$ | Z | $R_7$ | Yield (%) | mp (°C.) |
| --- | --- | --- | --- | --- | --- | --- | --- |
| IV-1 | $CH_3$ | $CH_3$ | $CH_2$-(4-Cl-C$_6$H$_4$) | O | $C_2H_5$ | 92 | 151~152 |
| IV-2 | $CH_3$ | $CH_3$ | $CH_2$-(2,6-Cl$_2$-C$_6$H$_3$) | O | $C_2H_5$ | 96 | 150~151 |
| IV-3 | $(CH_3)_2CH$ | H | $CH_2$-(2,4-Cl$_2$-C$_6$H$_3$) | O | $C_2H_5$ | 89 | 91~92 |
| IV-4 | $(CH_3)_2CH$ | H | $CH_2$-(2,4-Cl$_2$-C$_6$H$_3$) | O | $C_2H_5$ | 61 | 146~148 |
| IV-5 | H | $CH_3$ | $CH_2$-(2,4-Cl$_2$-C$_6$H$_3$) | O | $C_2H_5$ | 46 | 124~126 |
| IV-6 | cyclohexyl | | $CH_2$-(4-OCH$_3$-C$_6$H$_4$) | O | $C_2H_5$ | 60 | 153.5~154 |
| IV-7 | cyclohexyl | | $CH_2$-(4-CH$_3$-C$_6$H$_4$) | O | $C_2H_5$ | 65 | 147~149 |
| IV-8 | cyclohexyl | | $CH_2$-(2,4-Cl$_2$-C$_6$H$_3$) | O | $C_2H_5$ | 66 | 169~170 |
| IV-9 | cyclohexyl | | $(CH_2)_5CH_3$ | O | $C_2H_5$ | 77 | Oil |

Note: In IV-6 to IV-9, $R_1$ and $R_2$ together form a fused cyclohexyl ring.

TABLE 2-continued $$\text{(IV)}$$

Structure (IV): thiophene ring with $R_1$ at 5-position (S adjacent), $R_2$ at 4-position, C(=O)–N($R_3$) at 3-position forming a ring with N–CH$_2$COOR$_7$ attached to thiophene 2-position, and C=Z bridging the two nitrogens.

| No. | $R_1$ | $R_2$ | $R_3$ | Z | $R_7$ | Yield (%) | m.p. (°C) |
|---|---|---|---|---|---|---|---|
| IV″-10 | Br | CH$_3$ | CH$_2$–(2,4-dichlorophenyl) | O | C$_2$H$_5$ | 85 | 165.5~167 |
| IV″-11 | Cl | CH$_3$ | CH$_2$–(2,4-dichlorophenyl) | O | C$_2$H$_5$ | 65 | 141~145 |
| IV-12 | CH$_3$ | H | CH$_2$–(2-fluoro-4-bromophenyl) | O | C$_2$H$_5$ | 58 | 145~147 |
| IV-13 | phenyl | H | CH$_2$–(2-fluoro-4-bromophenyl) | O | C$_2$H$_5$ | 70 | 234~235 |
| IV-14 | CH$_3$ | CH$_3$ | CH$_2$–(2-fluoro-4-bromophenyl) | O | C$_2$H$_5$ | 88 | 144~146 |
| IV-15 | cyclohexyl | | CH$_2$–(2-fluoro-4-bromophenyl) | O | C$_2$H$_5$ | 60 | 141~143 |
| IV-16 | cyclopentyl | H | CH$_2$–(2-fluoro-4-bromophenyl) | O | C$_2$H$_5$ | 83 | 96~97 |
| IV-17 | (CH$_3$)$_2$CH | H | CH$_2$–(2-fluoro-4-bromophenyl) | O | C$_2$H$_5$ | 88 | 99~101 |
| IV-18 | (CH$_3$)$_3$C | H | CH$_2$–(2,4-dichlorophenyl) | O | C$_2$H$_5$ | 68 | 115~116 |
| IV-19 | H | H | CH$_2$–(2-fluoro-4-bromophenyl) | O | C$_2$H$_5$ | 63 | 117~119 |

TABLE 2-continued $$\text{(IV)}$$

Structure (IV): thiophene with $R_2$ at 4-position, $R_1$ at 5-position, S in ring; 3-position bears C(=O)–N(R_3)–C(=Z)–N(CH_2COOR_7) forming ring with 2-position N.

| Compound No. | $R_1$ | $R_2$ | $R_3$ | Z | $R_7$ | Yield (%) | mp (°C) |
|---|---|---|---|---|---|---|---|
| IV-20 | H | CH_3 | CH_2-(2-F,4-Br-C_6H_3) | O | C_2H_5 | 87 | 153~154 |
| IV-21 | (CH_3)_2CH | H | CH_2-(2-F,4-F-C_6H_3) | O | C_2H_5 | 50 | 111~112 |
| IV-22 | cyclopentyl | H | CH_2-(2-Cl,4-Cl-C_6H_3) | O | C_2H_5 | 73 | 135~136 |
| IV''-23 | Br | H | CH_2-(2-F,4-Br-C_6H_3) | O | C_2H_5 | 62 | 169~170 |
| IV'''-24 | Cl | H | CH_2-(2-F,4-Br-C_6H_3) | O | C_2H_5 | 93 | 132.5~133.5 |
| IV''''-25 | (CH_3)_2CH | H | CH_2-(2-F,4-Br-C_6H_3) | S | C_2H_5 | 85 | 177~179 |

| Compound No. | Molecular Formula | Elemental Analysis(%): Calcd. in parenthesis | | |
|---|---|---|---|---|
| | | C | H | N |
| IV-1 | $C_{19}H_{19}N_2O_4ClS$ | (56.09) | (4.71) | (6.88) |
| | | 55.84 | 4.50 | 6.89 |
| IV-2 | $C_{19}H_{18}N_2O_4Cl_2S$ | (51.71) | (4.11) | (6.35) |
| | | 51.42 | 4.19 | 6.14 |
| IV-3 | $C_{20}H_{20}N_2O_4Cl_2S$ | (52.75) | (4.43) | (6.15) |
| | | 52.85 | 4.45 | 6.15 |
| IV-4 | $C_{20}H_{20}N_2O_4Cl_2S$ | (52.75) | (4.43) | (6.15) |
| | | 52.86 | 4.44 | 6.11 |
| IV-5 | $C_{18}H_{16}N_2O_4Cl_2S$ | (50.60) | (3.77) | (6.56) |
| | | 50.70 | 3.77 | 6.62 |
| IV-6 | $CHN_2O_5S$ | (61.67) | (5.65) | (6.54) |
| | | 61.70 | 5.77 | 6.49 |
| IV-7 | $C_{22}H_{24}N_2O_4S$ | (64.06) | (5.86) | (6.79) |
| | | 64.14 | 5.81 | 6.75 |
| IV-8 | $C_{21}H_{20}Cl_2N_2O_4S$ | (53.97) | (4.31) | (5.99) |
| | | 53.80 | 4.32 | 5.99 |
| IV-9 | $C_{20}H_{28}N_2O_4S$ | (61.20) | (7.19) | (7.14) |
| | | 60.95 | 7.38 | 6.95 |
| IV'''-10 | $C_{18}H_{15}BrCl_2N_2O_4S$ | (47.21) | (2.99) | (5.53) |
| | | 47.50 | 2.84 | 5.42 |
| IV''-11 | $C_{18}H_{15}Cl_3N_2O_4S$ | (46.82) | (3.27) | (6.07) |
| | | 46.65 | 3.12 | 5.92 |
| IV-12 | $C_{18}H_{16}BrFN_2O_4S$ | (47.48) | (3.54) | (6.15) |
| | | 47.35 | 3.62 | 6.15 |
| IV-13 | $C_{23}H_{18}BrFN_2O_4S$ | (53.39) | (3.51) | (5.41) |
| | | 53.57 | 3.32 | 5.46 |
| IV-14 | $C_{19}H_{18}BrFN_2O_4S$ | (48.62) | (3.87) | (5.97) |
| | | 48.48 | 3.85 | 5.96 |

TABLE 2-continued $$\text{(IV)}$$

Structure (IV): thieno ring with R_1, R_2 substituents, S in ring, connected to pyrimidine with N-R_3, C=O, N-CH_2COOR_7, and =Z.

| | | | | |
|---|---|---|---|---|
| IV-15 | $C_{21}H_{20}BrFN_2O_4S$ | (50.92) | (4.07) | (5.66) |
| | | 50.70 | 4.09 | 5.60 |
| IV-16 | $C_{22}H_{22}BrFN_2O_4S$ | (51.87) | (4.35) | (5.50) |
| | | 52.35 | 4.42 | 5.47 |
| IV-17 | $C_{20}H_{20}BrFN_2O_4S$ | (49.70) | (4.17) | (5.80) |
| | | 49.77 | 4.31 | 5.72 |
| IV-18 | $C_{21}H_{22}Cl_2N_2O_4S$ | (53.74) | (4.72) | (5.97) |
| | | 53.70 | 4.85 | 6.07 |
| IV-19 | $C_{17}H_{14}BrFN_2O_4S$ | (46.27) | (3.20) | (6.35) |
| | | 46.35 | 3.32 | 6.18 |
| IV-20 | $C_{18}H_{16}BrFN_2O_4S$ | (47.48) | (3.54) | (6.15) |
| | | 47.50 | 3.54 | 6.18 |
| IV-21 | $C_{20}H_{20}F_2N_2O_4S$ | (56.86) | (4.77) | (6.63) |
| | | 56.46 | 5.10 | 6.77 |
| IV-22 | $C_{22}H_{22}Cl_2N_2O_4S$ | (54.89) | (4.61) | (5.82) |
| | | 55.06 | 4.56 | 5.86 |
| IV'''-23 | $C_{17}H_{13}Br_2FN_2O_4S$ | (39.25) | (2.52) | (5.39) |
| | | 39.28 | 2.60 | 5.21 |
| IV'''-24 | $C_{17}H_{13}BrClFN_2O_4S$ | (42.92) | (2.75) | (5.89) |
| | | 43.01 | 2.67 | 5.91 |
| IV''''-25 | $C_{20}H_{20}BrFN_2O_3S_2$ | (48.10) | (4.04) | (5.61) |
| | | 48.30 | 3.94 | 5.64 |

EXAMPLE 1

Preparation of 1-carboxymethyl-3-(4-chlorobenzyl)-5,6-dimethyl-thieno[2,3-d]pyrimidin-2,4(1H, 3H)-dione (Compound I-1)

A 0.7 g quantity of 3-(4-chlorobenzyl)-1-ethoxycarbonylmethyl-5,6-dimethylthieno[2,3-d]pyrimidin-2,4(1H, 3H)-dione (Compound IV-1) prepared in Reference Example 5 was dissolved in 30 ml of methanol. To the solution was added 0.3 g of sodium hydroxide dissolved in 2 ml of water. The mixture was allowed to react at 60° C. for 30 minutes, and then the reaction mixture was concentrated. Diluted hydrochloric acid was added thereto with ice-cooling to acidify the resulting solution. The solution was filtrated and the separated crystals were recrystallized from methanol, giving 0.4 g of 1-carboxymethyl-3-(4-chlorobenzyl)-5,6-dimethylthieno[2,3-d]pyrimidin-2,4(1H, 3H)-dione having m.p. of 173° to 176° C. in a yield of 61%.

| Elemental Analysis (for $C_{17}H_{15}N_2O_4SCl$) | | | |
|---|---|---|---|
| | C | H | N |
| Calcd. (%): | 53.90 | 3.99 | 7.39 |
| Found (%): | 53.75 | 4.04 | 7.31 |

EXAMPLE 2

The compounds I-2 to I-11 as shown below in Table 3 were prepared in the same manner as in Example 1.

EXAMPLE 3

Preparation of 1-carboxymethyl-3-(4-bromo-2-fluorobenzyl)-5-methyl-thieno[2,3-d]pyrimidin-2,4(1H, 3H)-dione (Compound I-20)

A 4.60 quantity of Compound IV-20 prepared in Reference Example 6, 20 ml of acetic acid and 10 ml of concentrated hydrochloric acid were refluxed for 4 hours, and then 10 ml of concentrated hydrochloric acid was added. The solution was further refluxed for 4 hours, and 10 ml of water was added. The mixture was allowed to stand overnight at room temperature. The crystals precipitated were collected, washed with water and recrystallized from 80% ethanol, giving 3.75 g of Compound I-20 having m.p. of 206.5° to 208° C. in a yield of 87%.

| Elemental Analysis (for $C_{16}H_{12}N_2O_4SBrF$) | | | |
|---|---|---|---|
| | C | H | N |
| Calcd. (%): | 44.98 | 2.83 | 6.56 |
| Found (%): | 45.02 | 2.78 | 6.38 |

EXAMPLE 4

The compounds I-12 to I-19 and I-21 to I-25 as shown below in Table 3 were prepared in the same manner as in Example 3.

EXAMPLE 5

Preparation of L-arginine salt of 1-carboxymethyl-3-(4-bromo-2-fluorobenzyl)-6-chloro-thieno[2,3-d]pyrimidin-2,4(1H,3H)-dione (Compound I-24)

A 0.45 g quantity of Compound I-24 was dissolved in 10 ml of ethanol with refluxing, and an aqueous solution (1 ml) of 0.174 g of L-arginine was added to the solution. Then the solution was cooled and allowed to stand at room temperature for one day. The crystals precipitated were collected, washed with ethanol and dried in vacuo at 100° C. for 6 hours, giving 0.49 g of the L-arginine salt of Compound I-24 having m.p. of 224° to 225.5° C. in a yield of 76%.

| Elemental Analysis (for $C_{21}H_{23}N_6O_6SBrClF$) | | | |
|---|---|---|---|
| | C | H | N |
| Calcd. (%): | 40.56 | 3.73 | 13.51 |
| Found (%): | 40.27 | 3.65 | 13.51 |

EXAMPLE 6

The L-lysine salt of Compound I-24 was prepared in the same manner as in Example 5 in a yield of 82%. M.p.: 213°–214° C.

| Elemental Analysis (for $C_{21}H_{23}N_4O_6SBrClF\cdot1H_2O$) | | | |
|---|---|---|---|
| | C | H | N |
| Calcd. (%): | 41.22 | 4.12 | 9.16 |
| Found (%): | 41.55 | 4.04 | 9.19 |

EXAMPLE 7

Preparation of 1-carboxymethyl-3-(4-bromo-2-flurobenzyl)-6-chloro-4(3H)-oxo-2(1H)-thioxothieno[2,3-d]pyrimidine (I-26)

According to the method described in Reference Example 12, 2.5 g of N-(4-bromo-2-fluorobenzyl)-5-chloro-2-ethoxycarbonylmethylamino-3-thiophenecarboxamide, 2.0 g of 1,1'-thiocarbonyldiimidazole and 20 ml of dioxane were mixed together and the mixture was allowed to react on a bath at a temperature of 150° C. for 2 hours. A 80 ml quantity of ethanol was added and the solution was cooled to room temperature. The crystals precipitated were collected to prepare 1.4 g of 1-ethoxycarbonylmethyl-3-(4-bromo-2-fluorobenzyl)-6-chloro-4(3H)-oxo-2(1H)-thioxothieno[2,3-d]pyrimidine as a crude product. This crude product was hydrolyzed in the same manner as in Example 3. That is, 15 ml of acetic acid and 15 ml of concentrated hydrochloric acid were added to this crude product, and the mixture was refluxed for 8 hours. Thereto 15 ml of water was added and the solution was cooled to room temperature. The crystals precipitated were collected by filtration and recrystallized from 80% ethanol, giving 0.54 g of 1-carboxymethyl-3-(4-bromo-2-fluorobenzyl)-6-chloro-4(3H)-oxo-2(1H)-thioxothieno[2,3-d]pyrimidine in a yield of 41%.

| Elemental Analysis (for $C_{15}H_9N_2O_3S_2BrClF$) | | | |
|---|---|---|---|
| | C | H | N |
| Calcd. (%): | 38.85 | 1.95 | 6.04 |
| Found (%): | 38.47 | 2.10 | 5.77 |

TABLE 3

(I)

structure with $R_1$, $R_2$ on thiophene ring fused to pyrimidinone with N-$R_3$, =Z, and N-CH$_2$COOH

| Compound No. | $R_1$ | $R_2$ | $R_3$ | Z | Yield (%) | mp (°C.) |
|---|---|---|---|---|---|---|
| I-1 | $CH_3$ | $CH_3$ | $CH_2$-C$_6$H$_4$-Cl (4-Cl) | O | 61 | 173~176 |
| I-2 | $CH_3$ | $CH_3$ | $CH_2$-C$_6$H$_3$-Cl$_2$ (2,4-diCl) | O | 53 | 266~267 |
| I-3 | $(CH_3)_2CH$ | H | $CH_2$-C$_6$H$_3$-Cl$_2$ (2,4-diCl) | O | 61 | 189~191 |
| I-4 | $(CH_3)_2CH$ | H | $CH_2$-C$_6$H$_3$-Cl$_2$ (2,4-diCl) | O | 44 | 228~229 |
| I-5 | H | $CH_3$ | $CH_2$-C$_6$H$_3$-Cl$_2$ (2,4-diCl) | O | 48 | >300 |

TABLE 3-continued

| | $R_1$ | $R_2$ | $R_3$ | Z | Yield (%) | mp (°C) |
|---|---|---|---|---|---|---|
| I-6 | cyclohexyl (fused) | | CH$_2$-C$_6$H$_4$-OCH$_3$ (p) | O | 65 | 230~234 |
| I-7 | cyclohexyl (fused) | | CH$_2$-C$_6$H$_4$-CH$_3$ (p) | O | 65 | 253~256 |
| I-8 | cyclohexyl (fused) | | CH$_2$-C$_6$H$_3$-2,4-Cl$_2$ | O | 63 | 265~266 |
| I-9 | cyclohexyl (fused) | | (CH$_2$)$_5$CH$_3$ | O | 65 | 204~206 |
| I-10 | Br | CH$_3$ | CH$_2$-C$_6$H$_3$-3,4-Cl$_2$ | O | 37 | >300 |
| I-11 | Cl | CH$_3$ | CH$_2$-C$_6$H$_3$-3,4-Cl$_2$ | O | 19 | >300 |
| I-12 | CH$_3$ | H | CH$_2$-C$_6$H$_3$-2-F-4-Br | O | 66 | 242~243 |
| I-13 | phenyl (fused) | H | CH$_2$-C$_6$H$_3$-2-F-4-Br | O | 71 | 249~251 |
| I-14 | CH$_3$ | CH$_3$ | CH$_2$-C$_6$H$_3$-2-F-4-Br | O | 80 | 233~235 |
| I-15 | cyclohexyl (fused) | | CH$_2$-C$_6$H$_3$-2-F-4-Br | O | 85 | 228~290 |

TABLE 3-continued (I)

structure: R2, R1 on thiophene (S) ring fused with N(CH2COOH)–C(=Z)–N(R3)–C(=O)–

| No. | R1 | R2 | R3 | Z | yield (%) | m.p. (°C) |
|---|---|---|---|---|---|---|
| I-16 | cyclopentyl | H | CH2–C6H3(2-F)(4-Br) | O | 49 | 160~162 |
| I-17 | (CH3)2CH | H | CH2–C6H3(2-F)(4-Br) | O | 55 | 203~205 |
| I-18 | (CH3)3C | H | CH2–C6H3(2-Cl)(4-Cl) | O | 67 | 194~197 |
| I-19 | H | H | CH2–C6H3(2-F)(4-Br) | O | 77 | 200~202 |
| I-20 | H | CH3 | CH2–C6H3(2-F)(4-Br) | O | 87 | 206.5~208 |
| I-21 | (CH3)2CH | H | CH2–C6H3(2-F)(4-F) | O | 75 | 194~196 |
| I-22 | cyclopentyl | H | CH2–C6H3(2-Cl)(4-Cl) | O | 34 | 222~226 |
| I-23 | Br | H | CH2–C6H3(2-F)(4-Br) | O | 93 | 244~246.5 |
| I-24 | Cl | H | CH2–C6H3(2-F)(4-Br) | O | 96 | 221~223 |
| I-25 | (CH3)2CH | H | CH2–C6H3(2-F)(4-Br) | S | 93 | 220~221 |

TABLE 3-continued $$\text{(I)}$$

Structure (I): thiophene ring with $R_1$, $R_2$ substituents, connected to a carbonyl group, N-R_3, and N(CH$_2$COOH) with =Z group.

| Compound No. | $R_1$ | $R_2$ | $R_3$ | Z | (other) | |
|---|---|---|---|---|---|---|
| I-26 | Cl | H | ![CH2-phenyl with F and Br](F, Br-phenyl-CH$_2$) | S | 41 | — |

I-26 $R_3$ group: -CH$_2$- attached to phenyl ring bearing F (ortho) and Br (para).

| Compound No. | Molecular Formula | Elemental Analysis (%): Calcd. in parenthesis | | |
|---|---|---|---|---|
| | | C | H | N |
| I-1 | $C_{17}H_{15}N_2O_4ClS$ | (53.90) | (3.99) | (7.39) |
| | | 53.75 | 4.04 | 7.31 |
| I-2 | $C_{17}H_{14}N_2O_4Cl_2S$ | (49.41) | (3.41) | (6.78) |
| | | 49.17 | 3.38 | 6.82 |
| I-3 | $C_{18}H_{16}N_2O_4Cl_2S$ | (50.60) | (3.77) | (6.56) |
| | | 50.62 | 3.91 | 6.54 |
| I-4 | $C_{18}H_{16}N_2O_4Cl_2S$ | (50.60) | (3.77) | (6.56) |
| | | 50.58 | 3.86 | 6.55 |
| I-5 | $C_{16}H_{12}N_2O_4Cl_2S$ | (48.13) | (3.03) | (7.02) |
| | | 48.10 | 2.98 | 7.12 |
| I-6 | $C_{20}H_{20}N_2O_5S$ | (59.99) | (5.03) | (7.00) |
| | | 60.11 | 5.14 | 7.03 |
| I-7 | $C_{20}H_{20}N_2O_4S$ | (62.48) | (5.24) | (7.29) |
| | | 62.61 | 5.17 | 7.32 |
| I-8 | $C_{19}H_{16}Cl_2N_2O_4S$ | (51.95) | (3.67) | (6.38) |
| | | 51.99 | 3.75 | 6.42 |
| I-9 | $C_{18}H_{24}N_2O_4S$ | (59.32) | (6.64) | (7.69) |
| | | 59.12 | 6.44 | 7.58 |
| I-10 | $C_{16}H_{11}N_2O_4BrCl_2S$ | (42.71) | (2.99) | (5.53) |
| | | 42.52 | 3.12 | 5.36 |
| I-11 | $C_{16}H_{11}N_2O_4Cl_3S$ | (44.31) | (2.56) | (6.46) |
| | | 44.22 | 2.38 | 6.34 |
| I-12 | $C_{16}H_{12}BrFN_2O_4S$ | (44.98) | (2.83) | (6.56) |
| | | 45.09 | 2.89 | 6.53 |
| I-13 | $C_{21}H_{14}BrFN_2O_4S$ | (51.55) | (2.88) | (5.72) |
| | | 51.13 | 3.09 | 5.43 |
| I-14 | $C_{17}H_{14}BrFN_2O_4S$ | (46.27) | (3.20) | (6.35) |
| | | 46.17 | 3.12 | 6.34 |
| I-15 | $C_{19}H_{16}BrFN_2O_4S$ | (48.83) | (3.45) | (5.99) |
| | | 48.70 | 3.41 | 6.03 |
| I-16 | $C_{20}H_{18}BrFN_2O_4S$ | (49.91) | (3.77) | (5.82) |
| | | 49.83 | 3.71 | 5.76 |
| I-17 | $C_{18}H_{16}BrFN_2O_4S$ | (47.48) | (3.54) | (6.15) |
| | | 47.25 | 3.83 | 6.17 |
| I-18 | $C_{21}H_{22}Cl_2N_2O_4S$ | (51.71) | (4.11) | (6.35) |
| | | 51.87 | 4.20 | 6.38 |
| I-19 | $C_{15}H_{10}BrFN_2O_4S$ | (43.60) | (2.44) | (6.78) |
| | | 43.55 | 2.50 | 6.67 |
| I-20 | $C_{16}H_{12}BrFN_2O_4S$ | (44.98) | (2.83) | (6.56) |
| | | 45.02 | 2.78 | 6.38 |
| I-21 | $C_{18}H_{16}F_2N_2O_4S$ | (54.82) | (4.09) | (7.10) |
| | | 55.32 | 4.17 | 7.13 |
| I-22 | $C_{20}H_{18}Cl_2N_2O_4S$ | (52.99) | (4.00) | (6.18) |
| | | 52.65 | 3.81 | 5.85 |
| I-23 | $C_{15}H_9Br_2FN_2O_4S$ | (36.61) | (1.84) | (5.69) |
| | | 36.80 | 1.82 | 5.61 |
| I-24 | $C_{15}H_9BrClFN_2O_4S$ | (40.24) | (2.03) | (6.26) |
| | | 40.63 | 1.96 | 6.28 |
| I-25 | $C_{18}H_{16}BrFN_2O_3S_2$ | (45.87) | (3.42) | (5.94) |
| | | 46.28 | 3.29 | 5.97 |
| I-26 | $C_{15}H_9BrClFN_2O_3S_2$ | (38.85) | (1.95) | (6.04) |
| | | 38.47 | 2.10 | 5.77 |

PHARMACOLOGICAL TEST

Pharmacological test was carried out on the compound (I) of the present invention as follows.

Aldose-Reductase Inhibitory Activity

The aldose-reductase (AR) activity was evaluated by determining spectrophotometrically the decrease in absorbance of NADPH at 340 nm due to the reduction of the substrate, i.e., glyceraldehyde according to the method described in Biochemical Pharmacology 25, pp 2505–2513 (1976).

The lenses of Wister male rats was homogenized with 0.5 ml of 0.1M phosphate buffer (pH 6.2) per lens by a glass homogenizer and the homogenate was centrifuged at 10000 rpm for 10 minutes. The supernatant obtained was used as AR.

The determination of the AR activity was conducted as follows. A 700 μl quantity of 0.1M phosphate buffer (pH 6.2), 100 μl of 2.21 mM NADPH, 100 μl of AR and 5 μl of DMSO containing each of test compounds in varying concentrations were placed in a cell for test sample, and 800 μl of 0.1M phosphate buffer (pH 6.2), 100 μl of 2.21 mM NADPH, 100 μl of AR and 5 μl of DMSO were placed in a cell for control. Then the solutions in the cells were thoroughly mixed together and the mixtures were maintained at 30° C. Then 100 μl of 100 mM glyceraldehyde maintained at 30° C. was added to a cell for test sample and quickly blended to initiate the reaction. The AR activity was determined from the rate of change of absorbance per minute in the linear part of variations of absorbance during a period of from 1 minute to three minutes after the start of the reaction, and a dose-response curve was drawn. An $IC_{50}$, i.e., a concentration exhibiting 50% inhibition, was calculated from the dose-response curve.

| Compound | $IC_{50}$ ($\times 10^{-8}$ mole/l) |
| --- | --- |
| I-1 | 7.5 |
| I-2 | 2.0 |
| I-3 | 2.6 |
| I-4 | 1.7 |
| I-5 | 3.0 |
| I-8 | 4.2 |
| I-10 | 2.6 |
| I-11 | 2.5 |
| I-13 | 3.4 |
| I-14 | 2.1 |
| I-15 | 2.3 |
| I-16 | 3.0 |
| I-17 | 2.2 |
| I-19 | 2.0 |
| I-20 | 2.4 |
| I-24 (Lysine salt) | 2.5 |

Preparation of pharmaceutical compositions containing the compounds of the present invention is described below in Preparation Examples.

PREPARATION EXAMPLE 1 (TABLETS)

A tablet was prepared from the following composition.

| Compound I-17 | 100 mg |
| --- | --- |
| Lactose | 47 mg |
| Corn starch | 50 mg |
| Crystalline cellulose | 50 mg |
| Hydroxypropyl cellulose | 15 mg |
| Talc | 2 mg |
| Magnesium stearate | 2 mg |
| Ethyl cellulose | 30 mg |
| Unsaturated fatty acid glyceride | 2 mg |
| Titanium dioxide | 2 mg |
| Total | 300 mg |

PREPARATION EXAMPLE 2 (CAPSULES)

An encapsulated preparation was formulated from the following composition.

| Compound I-24 | 50 mg |
| --- | --- |
| Lactose | 50 mg |
| Corn Starch | 47 mg |
| Crystalline cellulose | 50 mg |
| Talc | 2 mg |

| -continued | |
| --- | --- |
| Magnesium stearate | 1 mg |
| Total | 200 mg |

We claim:

1. A thienopyrimidine derivative of the formula

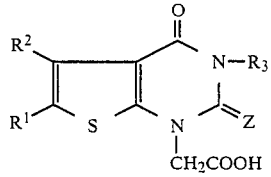

wherein $R_1$ and $R_2$ are the same or different and each represent hydrogen, halogen, lower alkyl, cycloalkyl or pheny, $R_1$ and $R_2$ taken together may form a ring with an alkylene chain, $R_3$ represents lower alkyl or a group of the formula

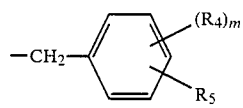

(in which $R_4$ is lower alkyl, lower alkoxy or halogen, m is 0, 1 or 2, and $R_5$ is hydrogen or halogen) and Z is oxygen or sulfur, or a pharmaceutically acceptable salt thereof.

2. A thienopyrimidine derivative or a pharmaceutically acceptable salt thereof as defined in claim 1 wherein $R_1$ is hydrogen, methyl, isopropyl or halogen, $R_2$ is hydrogen or methyl and $R_3$ is 3,4-dichlorobenzyl, 2,4-dichlorobenzyl or 4-bromo-2-fluorobenzyl and z is oxygen or sulfur.

3. A thienopyrimidine derivative or a pharmaceutically acceptable salt thereof as defined in claim 1 or 2 wherein $R_1$ is isopropyl, chlorine or bromine, $R_2$ is hydrogen and $R_3$ is 4-bromo-2-fluorobenzyl and z is oxygen.

4. A pharmaceutical composition comprising an effective amount of at least one thienopyrimidine derivative of the formula

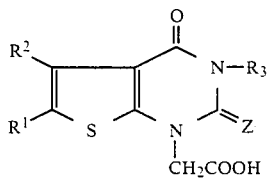

wherein $R_1$ and $R_2$ are the same or different and each represent hydrogen, halogen, lower alkyl, cycloalkyl or pheny, $R_1$ and $R_2$ taken together may form a ring with an alkylene chain, $R_3$ represents lower alkyl or a group of the formula

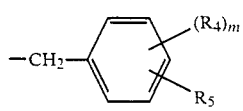

(in which $R_4$ is lower alkyl, lower alkoxy or halogen, m is 0, 1 or 2, and $R_5$ is hydrogen or halogen) and Z is oxygen or sulfur, or pharmaceutically acceptable salt thereof and a pharmaceutically acceptable carrier or excipient therefor.

5. An aldose-reductase inhibitor comprising an effective amount of at least one thienopyrimidine derivative of the formula

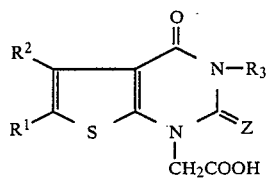

wherein $R_1$ or $R_2$ are the same or different and each represent hydrogen, halogen, lower alkyl, cycloalkyl or pheny, $R_1$ and $R_2$ taken together may form a ring with an alkylene chain, $R_3$ represents lower alkyl or a group of the formula

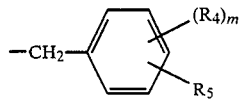

(in which $R_4$ is lower alkyl, lower alkoxy or halogen, m is 0, 1 or 2, and $R_5$ is hydrogen or halogen) and Z is oxygen or sulfur, or pharmaceutically acceptable salt thereof and a pharmaceutically acceptable carrier or excipient therefor.

* * * * *

UNITED STATES PATENT AND TRADEMARK OFFICE
CERTIFICATE OF CORRECTION

PATENT NO. : 4,898,867
DATED : February 6, 1990
INVENTOR(S) : OGAWA et al

It is certified that error appears in the above-identified patent and that said Letters Patent is hereby corrected as shown below:

On the cover page, Item [54] "DERIVATIES" should read

--DERIVATIVES--.

Column 1, line 1, "DERIVATIES" should read --DERIVATIVES--.

Signed and Sealed this

Twenty-eighth Day of May, 1991

*Attest:*

HARRY F. MANBECK, JR.

*Attesting Officer*  *Commissioner of Patents and Trademarks*